(12) United States Patent
Honda et al.

(10) Patent No.: US 11,021,499 B2
(45) Date of Patent: Jun. 1, 2021

(54) BIS(6-METHYL-3-SULPHOPHENYL) (2-METHYLPHENYL)PHOSPHINE, AMMONIUM SALT THEREOF, AND METHOD FOR PRODUCING SAME

(71) Applicants: KURARAY CO., LTD., Kurashiki (JP); HOKKO CHEMICAL INDUSTRY CO., LTD., Chuo-ku (JP)

(72) Inventors: Eriko Honda, Okayama (JP); Tatsuya Yoshikawa, Kamisu (JP); Tomoaki Tsuji, Kamisu (JP); Hitoshi Koizumi, Hiratsuka (JP); Kyoko Sugita, Atsugi (JP); Nobumichi Kumamoto, Atsugi (JP)

(73) Assignees: KURARAY CO., LTD., Kurashiki (JP); HOKKO CHEMICAL INDUSTRY CO., LTD., Chuo-ku (JP)

( * ) Notice: Subject to any disclaimer, the term of this patent is extended or adjusted under 35 U.S.C. 154(b) by 55 days.

(21) Appl. No.: 16/183,001

(22) Filed: Nov. 7, 2018

(65) Prior Publication Data

US 2019/0071460 A1 Mar. 7, 2019

Related U.S. Application Data

(63) Continuation of application No. 14/779,581, filed as application No. PCT/JP2014/058666 on Mar. 26, 2014, now abandoned.

(30) Foreign Application Priority Data

Mar. 27, 2013 (JP) .................................. 2013-067276

(51) Int. Cl.

| C07C 29/36 | (2006.01) |
|---|---|
| C07F 9/50 | (2006.01) |
| C07C 211/05 | (2006.01) |
| C07C 211/07 | (2006.01) |
| C07C 211/08 | (2006.01) |
| B01J 31/02 | (2006.01) |

(52) U.S. Cl.
CPC ......... *C07F 9/5022* (2013.01); *B01J 31/0225* (2013.01); *B01J 31/0267* (2013.01); *B01J 31/0271* (2013.01); *C07C 211/05* (2013.01); *C07C 211/07* (2013.01); *C07C 211/08* (2013.01); *B01J 2231/20* (2013.01)

(58) Field of Classification Search
None
See application file for complete search history.

(56) References Cited

U.S. PATENT DOCUMENTS

| 4,716,250 A | 12/1987 | Abatjoglou et al. |
| 5,057,631 A | 10/1991 | Tokitoh et al. |
| 5,114,473 A | 5/1992 | Abatjoglou et al. |
| 5,345,007 A | 9/1994 | Monflier et al. |
| 5,481,049 A | 1/1996 | Sato et al. |

FOREIGN PATENT DOCUMENTS

| CN | 1091117 A | 8/1994 |
| CN | 1096286 A | 12/1994 |
| GB | 2074156 A * | 10/1981 |
| JP | 63 88150 | 4/1988 |
| JP | 64 25739 | 1/1989 |
| JP | 3 232831 | 10/1991 |
| JP | 6 321828 | 11/1994 |
| JP | 8 501800 | 2/1996 |
| JP | 8 176167 | 7/1996 |
| JP | 2002 371088 | 12/2002 |
| JP | 2003 171388 | 6/2003 |
| WO | 95 39836 | 11/1995 |

OTHER PUBLICATIONS

Monflier et al. (Journal of Molecular Catalysis A: Chemical, vol. 97, 1995, 29-13 (Year: 1995).*
Combined Chinese Office Action and Search Report dated Jul. 18, 2016 in Patent Application No. 201480017402.0 (with English translators of categories of cited documents).
Ferreira et al., "Biphasic Aqueous Organometallic Catalysis Promoted by Cyclodextrins: How to Design the Water-Soluble Phenylphosphane to Avoid Interaction with Cyclodextrin", Advanced Synthesis & Catalysis, vol. 350, (2008), pp. 609-618.
Sayede et al., "Interaction of water-soluble triarylphosphines with β-cyclodextrin: a quantum chemistry study", Journal of Physical Organic Chemistry, vol. 24, No. 12, (2011), pp. 1129-1135.
Monflier et al., "Palladium catalyzed telomerization of butadiene with water in a two phase system: drastic effect of the amine structure on the rate and selectivity", Journal of Molecular Catalyasis A: Chemical, vol. 97, (1995), pp. 29-33.
Thorpe et al., "A practical synthesis of a disulfonated phosphine and its application to biphasic catalysis", Tetrahedron Letters, vol. 41, (2000), pp. 4503-4505.
Bhanage et al., "Selectivity in Sulfonation of Triphenyl Phosphine", Organic Process Research & Development, vol. 4, (2000), pp. 342-345.
Gulyas et al., "A direct approach to selective sulfonation of triarylphosphines", Tetrahedron Letters, vol. 43, No. 14, (2002), pp. 2543-2546.
International Search Report dated Jul. 1, 2014 in PCT/JP14/058666 Filed Mar. 26, 2014.

\* cited by examiner

*Primary Examiner* — Yun Qian
(74) *Attorney, Agent, or Firm* — Oblon, McClelland, Maier & Neustadt, L.L.P.

(57) ABSTRACT

Provided are a water-soluble triarylphosphine for a palladium catalyst, which has high selectivity in a telomerization reaction and is easily recovered with efficiency, an ammonium salt thereof, and a method for efficiently producing the same. Specifically, provided are bis(6-methyl-3-sulphophenyl)(2-methylphenyl)phosphine; a bis(6-methyl-3-sulphonatophenyl)(2-methylphenyl)phosphine diammonium salt obtained by reacting the phosphine with a tertiary amine having a total of 3 to 27 carbon atoms in groups bonded to one nitrogen atom; and a method for producing the same.

14 Claims, No Drawings

BIS(6-METHYL-3-SULPHOPHENYL)(2-METHYLPHENYL)PHOSPHINE, AMMONIUM SALT THEREOF, AND METHOD FOR PRODUCING SAME

CROSS REFERENCE TO RELATED APPLICATIONS

The present application is a continuation of application Ser. No. 14/779,581, filed on Sep. 24, 2015, which is a 35 U.S.C. § 371 national stage patent application of International patent application PCT/JP2014/058666, filed on Mar. 26, 2014, and claims the benefit of the filing date of Japanese application no. 2013-067276, filed on Mar. 27, 2013, the text of each of which is incorporated by reference.

TECHNICAL FIELD

The present invention relates to bis(6-methyl-3-sulphophenyl)(2-methylphenyl)phosphine, an ammonium salt thereof, and a method for producing the same.

BACKGROUND ART

A palladium catalyst comprised of a phosphorous compound and a palladium compound is useful as a catalyst for a telomerization reaction between two conjugated alkadiene molecules and a nucleophilic reactant. Specifically, it is useful as a catalyst for production of 2,7-octadien-1-ol by reacting two butadiene molecules with one water molecule in the presence of carbon dioxide and a tertiary amine to perform a telomerization reaction. 7-Octenal can be derived from 2,7-octadien-1-ol thus obtained by an isomerization reaction and 1,9-nonanedial can be derived from 7-octenal by a hydroformylation reaction. From the viewpoint that 1,9-nonanediamine which is useful as a raw material for a monomer for a polymer can be derived from 1,9-nonanedial by a reductive amination reaction, the 2,7-octadien-1-ol is of a high industrial value, and it is therefore important to develop a catalyst advantageous for the production thereof.

In order to produce 2,7-octadien-1-ol in an industrially advantageous manner, it is preferable to recover palladium as a noble metal in the telomerization reaction and reuse it in the reaction. As such a method for producing 2,7-octadien-1-ol, there are two methods using a telomerization reaction, as followings:

(A) a method for producing 2,7-octadien-1-ol, in which butadiene and water are subjected to a telomerization reaction in the presence of a palladium catalyst comprised of a palladium compound and a water-soluble phosphine in an aqueous sulfolane solution including a carbonate of a tertiary amine and a bicarbonate of a tertiary amine to generate 2,7-octadien-1-ol, at least part of the reaction mixed liquid is extracted with a saturated aliphatic hydrocarbon or the like to separate the 2,7-octadien-1-ol by extraction, and at least a part of the sulfolane eluent including the palladium catalyst is recycled and used in the reaction (see PTLs 1 to 3), and (B) a method for producing 2,7-octadien-1-ol, in which a tertiary amine having a function as a surfactant capable of compensating for a low reaction rate due to low solubility of butadiene in water coexists therewith in a two-phase system including an aqueous phase having a palladium catalyst comprised of a palladium compound and a water-soluble phosphorus-containing compound dissolved in water and an organic phase which is butadiene, and then butadiene and water are subjected to a telomerization reaction (see PTL 4 and NPL 1).

In the method (A), 2,7-octadien-1-ol is extracted by adding a saturated aliphatic hydrocarbon to a telomerization reaction liquid, and it is thus necessary to install equipment for distillation and recovery of the saturated aliphatic hydrocarbon, which results in an increase in cost burden associated with the equipment. Further, sulfolane is more expensive than ordinary hydrocarbon-based solvents, such as hexane, and accordingly, it is necessary to recover the sulfolane by subjecting the 2,7-octadien-1-ol phase obtained by extraction to washing with water, or the like, In addition, since sulfolane is a sulphur atom-containing substance, in a case of incineration disposal of sulfolane, an incinerator having desulphurization equipment is required. Therefore, there is a demand for a method for conveniently recovering most of a palladium catalyst after a telomerization reaction while not using sulfolane in the telomerization reaction.

In the method (B), dimethyldodecylamine, for example, is used as a tertiary amine. Since the dimethyldodecylamine has a function as a surfactant, complicated operations such as multiple extraction and recovery, or distillation and separation are required so as to increase the recovery of a tertiary amine. Further, according to Examples, it can be said that the method (B) is a method having low selectivity for 2,7-octadien-1-ol. Therefore, there is also a demand for a method in which the tertiary amine to be easily recovered can be used, and the selectivity for 2,7-octadien-1-ol is high.

Moreover, as a method for producing a water-soluble triarylphosphine which can be used in a telomerization reaction, the following methods are known:

(1) a method for producing a bis(3-sulphonatophenyl)phenylphosphine disodium salt, by dissolving triphenylphosphine in sulphuric acid, and then reacting the solution with sulphur trioxide in fuming sulphuric acid (see NPLs 2 and 3), (2) a method for producing a bis(3-sulphonatophenyl)phenylphosphine disodium salt by sulphonation of triphenylphosphine using an anhydrous mixture of sulphuric acid and orthoboric acid (see PTL 5), (3) a method in which triarylphosphine having an electron donating group such as a methyl group and a methoxy group in an aromatic ring is reacted with sulphur trioxide in the presence of sulphuric acid (see NPL 4), and (4) a method in which triarylphosphine having an electron donating group such as a methyl group and a methoxy group in each of three aromatic rings is reacted with sulphur trioxide in the presence of sulphuric acid (see NPL 5).

In the case of using the alkali metal salt of a triarylphosphine having a sulphonate group, obtained by these methods, in a telomerization reaction, there is a problem in that inorganic salts such as hydrogen carbonate of an alkali metal are accumulated in the reaction system, thus blocking pipes. It is known that as a method to avoid this problem, it is preferable to use an ammonium salt obtained by reacting a triarylphosphine having a sulphonate group with a tertiary amine as a catalyst for a telomerization reaction (see PTL 6).

In the method (1) for producing a water-soluble triarylphosphine, a bis(3-sulphonatophenyl)phenylphosphine disodium salt can be produced by sulphonating triphenylphosphine having a benzene ring as an equivalent aromatic ring relative to one phosphorus atom, bonded thereto with sulphur trioxide, followed by neutralization with sodium hydroxide, but the yield is as low as 60%. This is mainly caused by by-production of a tris(3-sulphonatophenyl)phosphine trisodium salt, indicating that it is difficult to selectively introduce only "two" sulpho groups with respect to the equivalent aromatic ring.

The method (2) for producing a water-soluble triarylphosphine is a method in which orthoboric acid is used instead of sulphur trioxide during a sulphonation reaction. The bis(3-sulphonatophenyl)phenylphosphine disodium salt is acquired with a yield of 94%, but in order to remove boric acid completely, toluene and triisooctylamine are added to a sulphonation reaction liquid once to cause a desired amine salt to be present in an organic phase, the organic phase is sufficiently washed with water, and the aqueous phase obtained by adding an aqueous sodium hydroxide solution to the washed organic phase is neutralized with sulphuric acid, and then concentrated. Then, methanol is added thereto to obtain a supernatant, from which methanol is removed, thereby acquiring a bis(3-sulphonatophenyl)phenylphosphine disodium salt. Although the yield is high, it is necessary to repeat washing to remove boric acid. Therefore, this method is difficult to carry out industrially.

The method (3) for producing a water-soluble triarylphosphine is a method in which a triaryiphosphine in which an electron donating group such as a methyl group and a methoxy group is introduced in advance to an aromatic ring is reacted with sulphur trioxide in the presence of sulphuric acid. The method simply shows that only in the case where a triarylphosphine having a non-equivalent aromatic ring such as bis(4-methoxyphenyl)phenylphosphine or the like is used as a raw material, the number of the introduced sulpho groups of the bis(4-methoxy-3-sulphonatophenyl)phenylphosphine disodium salt or the like can be controlled, but does not show that the number of the introduced sulpho groups in tris(2-methylphenyl)phosphine having an equivalent aromatic ring can be controlled.

The method (4) for producing a water-soluble triarylphosphine shows that a bis(6-methyl-3-sulphonatophenyl)(2-methylphenyl)phosphine disodium salt can be acquired, but does not disclose specific production methods and yields thereof, which means the method simply shows the probability of isolating the present compound.

As a method for producing an ammonium salt of a triarylphosphine having a sulphonate group, methods in which an alkali metal salt of a triarylphosphine having a sulphonate group is used as a raw material, a counter-cation is converted into a desired ammonium salt by an ion exchange process in the following manner are known. The methods are as follows:

a method in which sulphuric acid is added to an aqueous solution of a diphenyl(3-sulphonatophenyl)phosphine sodium salt, 4-methyl-2-pentanone is then added thereto, and triethylamine is added to the obtained organic phase, thereby precipitating a solid-state diphenyl(3-sulphonatophenyl)phosphine triethylammonium salt (see PTL 6); and a method in which a diphenyl(3-sulphonatophenyl)phosphine sodium salt is pressurized with carbon dioxide in the presence of triethylamine, ethanol, and 2-propanol, and a desired product is acquired from a filtrate of the reaction liquid (see PTL 7).

CITATION LIST

Patent Literature

[PTL 1] JP-A-64-25739
[PTL 2] JP-A-3-232831
[PTL 3] JP-A-6-321828
[PTL 4] JP-T-8-501800
[PTL 5] JP-A-8-176167
[PTL 6] JP-A-2002-371088
[PTL 7] JP-A-2003-171388

Non Patent Literature

[NPL 1] Journal of Molecular Catalysis A: Chemical, vol. 97, 1995, pp. 29 to 33
[NPL 2] Tetrahedron Letters, 2000, vol. 41, pp. 4503 to 4505
[NPL 3] Organic Process Research & Development, 2000, vol. 4, pp. 342 to 345
[NPL 4] Tetrahedron Letters, vol. 43, 2002, pp. 2543 to 2546
[NPL 5] Advanced Synthesis & Catalysis, 2008, vol. 350, pp. 609 to 618

SUMMARY OF INVENTION

Technical Problem

In the ion exchange method described in PTL 6, according to the investigations of the present inventors, bis(6-methyl-3-sulphophenyl)(2-methylphenyl)phosphine was insufficiently extracted with an acyclic ketone solvent, and therefore, the yield was as low as 30% or less.

In the ion exchange method described in PTL 7, according to the investigations of the present inventors, when the same operation was carried out using a bis(6-methyl-3-sulphonatophenyl)(2-methylphenyl)phosphine disodium salt, the ion exchange rate of the counter-cation was as low as 20% or less.

Therefore, it is an object of the present invention to provide a water-soluble triarylphosphine for a palladium catalyst, which has high selectivity in a telomerization reaction and is easily recovered with efficiency, and a method for producing the same efficiently.

Solution to Problem

The present inventors have conducted extensive studies, and as a result, they have found that the selectivity for desired products is increased in a telomerization reaction of two molecules of an alkadiene such as butadiene with a nucleophilic reactant such as water by using a palladium catalyst comprised of a specific ammonium salt of bis(6-methyl-3-sulphophenyl)(2-methylphenyl)phosphine and a palladium compound. Further, they have also found that in the case of using the palladium catalyst in a telomerization reaction, products can be extracted from the organic phase by adding an organic solvent having a specific dielectric constant to the obtained telomerization reaction liquid, while recovery of the palladium catalyst from the aqueous phase can be carried out with high yield, thereby completing the present invention.

That is, the present invention relates to [1] to [7] below.

[1] Bis(6-methyl-3-sulphophenyl)(2-methylphenyl)phosphine.

[2] A bis (6-methyl-3-sulphonatophenyl)(2-methylphenyl)phosphine diammonium salt obtained by reacting the bis(6-methyl-3-sulphophenyl)(2-methylphenyl)phosphine according to [1] with a tertiary amine having a total of 3 to 27 carbon atoms in groups bonded to one nitrogen atom.

[3] The bis(6-methyl-3-sulphonatophenyl)(2-methylphenyl)phosphine diammonium salt according to [2], wherein the tertiary amine is trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, N,N-dibenzylmonoethylamine, or trinonylamine.

[4] A mixture comprising 5% by mole or less of bis(2-methylphenyl)(6-methyl-3-sulphophenyl)phosphine, 80% by mole or more of bis(6-methyl-3-sulphophenyl)(2-methylphenyl)phosphine, and 15% by mole or less of tris(6-methyl-3-sulphophenyl)phosphine.

[5] A mixture containing 80% by mole or more of a bis(6-methyl-3-sulphonatophenyl)(2-methylphenyl)phosphine diammonium salt obtained by reacting the mixture according to [4] with a tertiary amine having a total of 3 to 27 carbon atoms in groups bonded to one nitrogen atom.

[6] A method for producing bis(6-methyl-3-sulphophenyl)(2-methylphenyl)phosphine, having: a step of reacting 2.5 moles to 4.5 moles of sulphur trioxide with 1 mole of tris(2-methylphenyl)phosphine in the presence of concentrated sulphuric acid to obtain a sulphonation reaction liquid, and diluting the obtained sulphonation reaction liquid with water to obtain a diluted liquid; a step of neutralizing the diluted liquid with an alkali metal hydroxide; and a step of bringing the aqueous solution obtained in the neutralization step into contact with a strongly acidic cation exchange resin.

[7] A method for producing a bis(6-methyl-3-sulphonatophenyl)(2-methylphenyl)phosphine diammonium salt by reacting bis(6-methyl-3-sulphophenyl)(2-methylphenyl)phosphine with a tertiary amine having a total of 3 to 27 carbon atoms in groups bonded to one nitrogen atom.

Advantageous Effects of Invention

According to the present invention, high selectivity in a telomerization reaction, can be accomplished by using a water-soluble triarylphosphine for a palladium catalyst, and the palladium catalyst after use can be efficiently recovered. Further, a water-soluble triarylphosphine, which will be a raw material for a palladium catalyst, can be selectively produced by the production method of the present invention.

DESCRIPTION OF EMBODIMENTS

First, in the present specification, the restrictive wording with "being preferable" can be arbitrarily adopted, and a combination of restrictive wordings with "being preferable" can be said to be more preferred.

The present invention provides bis(6-methyl-3-sulphophenyl)(2-methylphenyl)phosphine and an ammonium salt thereof. The ammonium salt thereof is more specifically a bis(6-methyl-3-sulphonatophenyl)(2-methylphenyl)phosphine diammonium salt.

These can be produced efficiently by the following steps, but the invention is not particularly limited to the following steps.

1. Sulphonation Step

A step of reacting 2.5 moles to 4.5 moles of sulphur trioxide with 1 mole of tris(2-methylphenyl)phosphine in the presence of concentrated sulphuric acid to obtain a sulphonation reaction liquid, and diluting the obtained sulphonation reaction liquid with water to obtain a diluted liquid is included.

2. Neutralization Step

A step of neutralizing the diluted liquid with an alkali metal hydroxide to obtain an aqueous solution including a bis(6-methyl-3-sulphonatophenyl)(2-methylphenyl)phosphine dialkali metal salt.

3. Ion Exchange Step

A step of bringing the aqueous solution obtained in the neutralization step into contact with a strongly acidic cation exchange resin to form bis(6-methyl-3-sulphophenyl)(2-methylphenyl)phosphine.

The bis(6-methyl-3-sulphophenyl)(2-methylphenyl)phosphine can be produced by the steps hitherto described. Further, for the production of a bis(6-methyl-3-sulphonatophenyl)(2-methylphenyl)phosphine diammonium salt, the following steps are further required.

4. Ammonium Salt Forming Step

A step of reacting bis(6-methyl-3-sulphophenyl)(2-methylphenyl)phosphine with a tertiary amine having a total of 3 to 27 carbon atoms in groups bonded to one nitrogen atom to form a bis(6-methyl-3-sulphonatophenyl)(2-methylphenyl)phosphine diammonium salt.

Furthermore, the steps will be described in detail below, but from the viewpoint that the phosphine compound is easily oxidized by oxygen, although not being clearly described, operations in the steps are carried out in an inert gas atmosphere in principle. Furthermore, from the same viewpoint, in the case of using a solvent, it is preferable to use a solvent having dissolved oxygen included in the solvent is purged with an inert gas. Examples of the inert gas include nitrogen, helium, and argon, and from the viewpoint of high industrial availability, it is preferable to use nitrogen gases.

1. Sulphonation Step

The method for producing tris(2-methylphenyl)phosphine is not particularly limited, and the tris(2-methylphenyl) phosphine can be produced according to a known method. For example, a reaction of phosphorous trichloride with a Grignard reagent obtained from 2-bromotoluene (see Journal of Organic Chemistry, 1978, vol. 43, pp. 2941 to 2956) and the like are known.

Furthermore, as the tris(2-methylphenyl)phosphine, those that are commercially distributed can be used, and for example, "TOTP" (registered trademark) manufactured by Hokko Chemical Industry Co., Ltd., and the like can be purchased and used.

The operation sequence in the reaction of tris(2-methylphenyl)phosphine with sulphur trioxide in the presence of concentrated sulphuric acid is not particularly limited, but for example, tris(2-methylphenyl)phosphine can be sulphonated by dissolving tris(2-methylphenyl)phosphine in concentrated sulphuric acid, followed by reaction with sulphur trioxide.

Furthermore, sulphonation can also be carried out by the reaction with orthoboric acid instead of sulphur trioxide. According to the findings, of the present inventors, in the case of using orthoboric acid, from the viewpoint that the removal of orthoboric acid from the sulphonation reaction liquid is complicated, it is preferable to use sulphur trioxide, and it is more preferable to use fuming sulphuric acid including sulphur trioxide and sulphuric acid.

The sulphonation step can be carried out using a continuous stirred tank reactor equipped with a jacket. The continuous stirred tank reactor as mentioned herein is a reactor designed such that raw materials supplied to the reactor are mixed in a substantially homogeneous dispersion state without any delay.

The material for the reactor is preferably stainless steel, Hastelloy C, titanium, or the like, and further, as a material for an inner wall of a reactor, a glass-lined material may be used. From the viewpoint of avoiding the incorporation of metal ions originating from the reactor into a desired product, it is preferable to use glass-lined material for the inner wall. Further, the glass lining process is a method in which two materials, a metal and glass, are fused to perform surface modification of the metal.

The sulphonation step can be carried out in any of a batch mode (including a semi-continuous mode) and a flow and continuous mode. In some cases, it can also be carried out in a flow and continuous mode by connecting two or three continuous stirred tank reactors in series. From the viewpoint that simplification of equipment results from dilution of a sulphonation reaction liquid with water as described later and the subsequent neutralization step, both carried out in one reaction tank, it is preferable to carry out, the process in a batch mode (including a semi-continuous mode).

Concentrated sulphuric acid serves to dissolve tris(2-methylphenyl)phosphine. As the concentrated sulphuric acid, one having a high content of sulphuric acid is preferred, and from the viewpoint of industrial availability, one having a concentration of 96% by mass or more is more preferably used. A higher content of sulphuric acid in concentrated sulphuric acid is preferable since it can inhibit the hydrolysis of sulphur trioxide in fuming sulphuric acid. From the viewpoint that fuming sulphuric acid is more expensive than sulphuric acid, it is economically preferable to inhibit the hydrolysis of sulphur trioxide.

Since concentrated sulphuric acid used for sulphonation is generally subjected to a disposal treatment by forming a sulphuric acid alkali metal salt by neutralization with an alkali metal hydroxide or the like, production conditions for reducing the amount of sulphuric acid used are preferred. From this viewpoint, the amount of sulphuric add used is preferably about an amount which allows tris(2-methylphenyl)phosphine to be dissolved, and more preferably an amount which adjusts the amount of tris(2-methylphenyl) phosphine to be from 20% by mass to 70% by mass. Within this range, the amount of sulphuric acid to be disposed of can be reduced, it becomes possible to perform a reaction with sulphur trioxide in a sufficiently mixed state due to low viscosity of the prepared mixed solution, and in addition, the yield of the desired product is enhanced.

The temperature at a time of preparation of a concentrated sulphuric acid solution of tris(2-methylphenyl)phosphine is preferably from 0° C. to 100° C., and more preferably from 20° C. to 40° C. Within this range, the oxidation reaction of tris(2-methylphenyl)phosphine does not proceed, it becomes possible to perform a reaction with sulphur trioxide in a sufficiently mixed state due to low viscosity of the prepared mixed solution, and in addition, the yield of the desired product is enhanced.

Sulfur trioxide is preferably used for the reaction in the form of a fuming sulphuric acid in which sulphur trioxide is dissolved in sulphuric acid. The concentration of sulphur trioxide in fuming sulphuric acid is preferably from 10% by mass to 60% by mass, and more preferably from 20% by mass to 50% by mass. Within this range, the amount of sulphuric acid practically used can be reduced, and the time required for the sulphonation step can be shortened due to a fact that the sulphur trioxide concentration in the reaction system can be maintained at a certain level or higher.

The amount of sulphur trioxide used is preferably from 2.5 moles to 4.5 moles, and more preferably from 3.0 moles to 4.0 moles, with respect to one mole of phosphorous atoms contained in tris(2-methylphenyl)phosphine. Within this range, the yield of the desired product is high. Further, the numerical value range is a numerical value not considering the consumption by hydrolysis. In the case where consumption by hydrolysis is considered, it is preferable to increase the amount of sulphur trioxide used according to the amount.

The reaction temperature for the sulphonation step is preferably from 0° C. to 100° C., more preferably from 10° C. to 50° C., and still more preferably from 20° C. to 50° C. Within this range, even in the state where the reaction time is short, the yield of a desired product is high.

It is preferable to add fuming sulphuric acid to a concentrated sulphuric acid solution of tris(2-methylphenyl)phosphine slowly, and the time taken for the addition is preferably from 0.25 hours to 5 hours, and more preferably from 0.5 hours to 3 hours. Within this range, the reaction time is not too long, and the yield of a desired product is high. Further, it is preferable that after the addition of fuming sulphuric acid, the flow path of the fuming sulphuric acid is washed with concentrated sulphuric acid, and a washing liquid thus obtained is mixed with the reaction solution.

The reaction time after the completion of addition of fuming sulphuric acid is preferably from 2 hours to 20 hours, and more preferably from 2 hours to 8 hours. In the case of this range, the yield of a desired product is high.

Water Dilution Operation

Unreacted sulphur trioxide can be hydrolyzed by diluting the sulphonation reaction liquid obtained by the operation above with water, whereby it is possible to stop the sulphonation reaction.

Furthermore, water used for the dilution serves to remove the dilution heat of concentrated sulphuric acid and the hydrolysis reaction heat of sulphur trioxide, and also serves as a solvent in the neutralization step of the next step.

The temperature of water used for dilution may be any temperature at which water does not freeze, and it is preferably from 1° C. to 40° C., and more preferably from 2° C. to 25° C. Among the temperatures in this range, a lower temperature is preferred since heat can be efficiently removed.

The amount of water used may be at least any amount in which unreacted sulphur trioxide can be hydrolyzed, but from the viewpoint of control of the temperature in the neutralization step as described later, it is from 1 time to 20 times by mass that of the sulphonation reaction liquid. Within this range, heat removal is easy and the amount of waste water in the neutralization step as described later can be reduced.

The liquid temperature at the time of dilution with water is preferably from 0° C. to 100° C., and more preferably from 1° C. to 40° C. Within this range, operations such as lowering the temperature of the liquid at a time of starting the neutralization step are not required, and thus, the productivity can be improved.

2. Neutralization Step

In the neutralization step, the reactor used in the sulphonation step is used as it is, and further, it is preferable to continuously carry out the step in a is batch mode (including a semi-continuous mode) from the viewpoint of simplification of equipment.

Examples of the alkali metal hydroxide used in the neutralization step include lithium hydroxide, sodium hydroxide, and potassium hydroxide. Among these, potassium hydroxide and sodium hydroxide are preferred, and sodium hydroxide is more preferred.

By using the alkali metal hydroxide, a high ion exchange rate from bis(6-methyl-3-sulphonatophenyl)(2-methylphenyl)phosphine dialkali metal salt to bis(6-methyl-3-sulphophenyl)(2-methylphenyl)phosphine with a strongly acidic cation exchange resin can be accomplished.

The alkali metal hydroxide may be used in the form of a solid and may be used as an aqueous solution. However, from the viewpoints of avoiding local heat generation at a time of neutralization and increasing the heat removal efficiency, the alkali metal hydroxide is preferably used as an aqueous solution. The concentration of the aqueous alkali metal hydroxide solution is not particularly limited, and the aqueous alkali metal hydroxide solution is preferably used at a concentration of 10% by mass to 50% by mass, and more preferably used at a concentration of 20% by mass to 40% by mass. Within this range, the liquid amount after the neutralization is low, and thus, the amount of waste water can be reduced. Further, it is preferable that the aqueous alkali metal hydroxide solution is slowly added to the sulphonation reaction liquid obtained in the sulphonation step, and in some cases, the aqueous alkali metal hydroxide solution can be added in several separate portions. Further, after using the aqueous alkali metal hydroxide solution in the concentration range, aqueous alkali metal hydroxide solutions having different concentrations, for example, an aqueous alkali metal hydroxide solution (usually an aqueous alkali metal hydroxide solution having a low concentration) having a concentration out of the range may be used later.

The amount of alkali metal hydroxide used is not particularly limited as long as it can neutralize sulphuric acid and bis(6-methyl-3-sulphophenyl)(2-methylphenyl)phosphine, and it is preferably an amount such that the pH of the aqueous solution at 25° C. after the completion of neutralization is preferably from 7.0 to 9.5, and more preferably from 7.5 to 8.5. Within this range, most of sulphuric acid can be induced to a sulphuric acid alkali metal salt. Further, excess alkali metal hydroxide can be converted to water in the ion exchange step as described later.

The neutralization temperature is not particularly limited, and usually, it is preferably from 0° C. to 40° C., and more preferably from 1° C. to 25° C. in order to promote desirable precipitation of alkali metal sulphate. When the neutralization temperature is 0° C. or higher, the amount of energy consumed, relevant to cooling, can be reduced, which is thus preferable. Further, when the neutralization temperature is 40° C. or lower, precipitation of the alkali metal sulphate during the transportation of the liquid can be inhibited, and therefore, there is no concern about pipes becoming blocked.

The time required for the neutralization is any time as long as it is in a range suitable for the heat removal ability of a reactor used. Specifically, the time is preferably from 0.5 hours to 20 hours, and more preferably from 2 hours to 5 hours. When the time is 0.5 hours or longer, it is possible to remove neutralization heat efficiently. As a result, it is economically advantageous since it is not necessary to use a continuous stirred tank with high efficiency in heat removal. When the time is 20 hours or shorter, the increase in the amount of energy consumed for maintenance of the set temperature can be inhibited, which is thus preferable.

The aqueous solution formed by the neutralization in the present step (hereinafter referred to as a neutralized liquid) has a bis(6-methyl-3-sulphonatophenyl)(2-methylphenyl)phosphine dialkali metal salt and an alkali metal sulphate as a main component.

The solubility in an alcohol, such as methanol, ethanol, and 1-propanol, of the bis(6-methyl-3-sulphonatophenyl)(2-methylphenyl)phosphine dialkali metal salt is higher than that of the alkali metal sulphate, and thus, by using the difference in solubility, the alkali metal sulphate can be separated out. Although it is possible to precipitate the alkali metal sulphate by directly adding an alcohol to the neutralized liquid, it is preferable to evaporate as much water as possible from the neutralized liquid in advance, and it is more preferable to evaporate 90% by mass to 98% by mass of the water in the neutralized liquid, from the viewpoints of reducing the amount of alcohol used and inhibiting the incorporation of the alkali metal sulphate into a desired product. In this manner, an approach in which the alcohol is added to a concentrate obtained by evaporating water to separate out the alkali metal sulphate is preferred.

Examples of the alcohol include methanol, ethanol and 1-propanol, and from the viewpoint of reducing the amount of the alcohol, it is preferable to use methanol.

The amount of the alcohol used for the separation of the alkali metal sulphate is not particularly limited, and is preferably from 0.5-fold by mass to 80-fold by mass, and more preferably from 5-fold by mass to 20-fold by mass, with respect to the concentrate. Within this range, at a time of isolation of a desired product, the amount of alcohol evaporated can be reduced, and further, the alkali metal salt can be sufficiently precipitated.

An insoluble material of the alcohol solution is the alkali metal sulphate, which may be separated and removed by filtration or decantation. The temperature for filtration or decantation is preferably from 0° C. to 50° C., and more preferably from 1° C. to 25° C. Within this range, it is possible to precipitate only the alkali metal sulphate selectively, and thus, the yield of a desired product is high.

In the case where the alkali metal sulphate is incorporated into the alcohol solution obtained as described above, the obtained alcohol solution may be concentrated and be dissolved in an alcohol again to repeat the operation for separation and removal of the alkali metal sulphate.

By evaporating the alcohol from the alcohol solution, it is possible to acquire a mixture of 5% by mole or less of a bis(2-methylphenyl)(6-methyl-3-sulphonatophenyl)phosphine alkali metal salt, 80% by mole or more of a bis(6-methyl-3-sulphonatophenyl)(2-methylphenyl)phosphine dialkali metal salt, and 15% by mole or less of a tris(6-methyl-3-sulphonatophenyl)phosphine trialkali metal salt as a solid. This mixture will be hereinafter abbreviated as a mixture of alkali metal salts.

In order to increase the content of the bis(6-methyl-3-sulphonatophenyl)(2-methylphenyl)phosphine dialkali metal salt in the mixture of alkali metal salts, column chromatography using a mixed solvent including water, tetrahydrofuran, and the like as a mobile phase, which is passed through columns packed with silica gel, can be used. Alternatively, a method in which an aqueous solution of a mixture of alkali metal salts is prepared and washed with an organic solvent such as 2-butanone can also be used.

3. Ion Exchange Step

By reacting the mixture of alkali metal salts obtained in the neutralization step with a strongly acidic cation exchange resin, bis(6-methyl-3-sulphophenyl)(2-methylphenyl)phosphine can be derived from the bis(6-methyl-3-sulphonatophenyl)(2-methylphenyl)phosphine dialkali metal salt.

According to the investigations of the present inventors, in a known method including reacting a triarylphosphine in which a counter-cation of a sulpho group is an alkali metal with a tertiary amine and carbon dioxide in the presence of an alcohol solvent, and a known method including reacting a triarylphosphine in which a counter-cation of a sulpho group is an alkali metal with a protonic acid in a solvent such as an acyclic ketone, the yield of a desired product is lowered in any case. Therefore, it is crucial to use a strongly acidic ion exchange resin, and according to the method, the yield of a desired product is increased.

It is also possible to bring an alcohol solution of the mixture of alkali metal salts as it is into contact with a strongly acidic cation exchange resin, but since the solubility of the mixture of alkali metal salts in an alcohol is lower than that in water, it is preferable to bring the mixture of alkali metal salts from an aqueous solution into contact with a strongly acidic cation exchange resin to undergo a reaction.

By using a strongly acidic cation exchange resin as a cation exchange resin, the alkali metal ions can be sufficiently converted to protons even with a small amount of the ion exchange resin.

As the strongly acidic cation exchange resin, those in which a sulpho group is introduced to a copolymer of styrene and divinylbenzene, a copolymer of perfluorosulphonic acid and tetrafluoroethylene, and the like can be preferably used.

Examples of the strongly acidic cation exchange resin include those which are non-aqueous and aqueous, either of which may be used. According to the kind of a substrate, a macroporous type substrate, a gel type substrate, and the like can be mentioned, either of which may be used. As the strongly acidic cation exchange resin, those in which the counterion of a sulpho group contained in the resin is a proton or a sodium ion are generally known. In the case where the counterion is a sodium ion, the sodium ion is converted into a proton by carrying out a pre-treatment with a protonic acid such as hydrochloric acid and sulphuric acid, then the pretreated resin is used. In the case of a resin in which the counterion is a proton, it can be used without a pre-treatment.

The strongly acidic cation exchange resin may have a powder shape or particulate shape, but from the viewpoint of avoiding damage due to friction in the state of use, it is preferable to use a resin having a particulate shape. In the case of using a resin having a particulate shape, the average particle diameter is not particularly limited, and is preferably from 0.3 mm to 3 mm, and more preferably from 0.5 mm to 1.5 mm. When the average particle diameter is 0.3 mm or more, it is difficult for the resin to be incorporated into a product, whereas when the average particle diameter is 3 mm or less, a large contact area of the resin with the aqueous solution of the mixture of alkali metal salts can be maintained, and as a result, the amount of the strongly acidic cation exchange resin used can be reduced.

Examples of the strongly acidic cation exchange resin formed by introducing a sulpho group into a copolymer of styrene and divinylbenzene, which satisfies the above, include Amberlyst 15, Amberlyst 16, Amberlyst 31, Amberlyst 32, and Amberlyst 35 [in which Amberlyst is a registered trademark], all manufactured by Rohm and Haas Company, Dowex 50W, Dowex 88, and Dowex G-26 [in which Dowex is a registered trademark], all manufactured by Dow Chemical Company, and Diaion SK104, Diaion SK1B, Diaion PK212, Diaion PK216, and Diaion PK228 [in which Diaion is a registered trademark], all manufactured by Mitsubishi Chemical Corporation.

Examples of the strongly acidic cation exchange resin as a copolymer of perfluorosulphonic acid and tetrafluoroethylene include Nafion SAC-13 and Nafion NR-50 [in which Nafion is a registered trademark], both manufactured by E. I. du Pont de Nemours and Company.

The strongly acidic cation exchange resins may be used alone or in combination of two or more kinds thereof.

The ion exchange step can be carried out in either a flow mode or a batch mode. In the case of carrying out in a flow mode using a column, a fixed bed reactor, or the like, damage due to the friction of the strongly acidic cation exchange resin can be inhibited, and further, there is an effect that the equilibrium reaction is biased, whereby the amount of the strongly acidic cation exchange resin used can be reduced.

From the viewpoint of making the flow of the aqueous solution uniform, it is preferable that the reactor has a tubular structure. The tube diameter is not particularly limited, but it is preferably from 50 mm to 500 mm from the viewpoint of making the exchange operation of the strongly acidic cation exchange resin convenient. The length and number of the reactor tube as a reactor are not particularly limited, but are preferably appropriately set from the viewpoint of the production cost, strongly acidic cation exchange resin and the like, which the resin is required to achieve a desired production capacity of the reactor.

In addition, the laminar flow may be in a down-flow mode for supplying the aqueous solution from the top of a reactor or an upflow mode for supplying from the bottom of a reactor when the reactor is a fixed bed reactor.

The concentration of the mixture of alkali metal salts in the aqueous solution of the mixture of alkali metal salts is preferably from 1% by mass to 30% by mass, and more preferably from 5% by mass to 20% by mass. Within these ranges, it is possible to convert 99% by mole or more of the alkali metal ions into protons even with a small amount of water used.

The temperature of the aqueous solution of the mixture of alkali metal salts is preferably from 10° C. to 120° C., and more preferably from 15° C. to 40° C. If the temperature is 10° C. or higher, there is no reduction in the ion exchange rate, and the increase in the amount of the strongly acidic cation exchange resin used can be avoided. Further, if the temperature is 120° C. or lower, the pores of the resin can be inhibited from being closed by the deformation of the ion exchange resin, and in addition, the reduction in the rate of ion exchange can be inhibited.

The amount of the strongly acidic cation exchange resin used preferably corresponds to 1.5 times or more the theoretical ion-exchangeable amount which is calculated from the amount of the alkali metal ions to be preliminarily exchanged. By this, it is possible to exchange 99% by mole or more of the alkali metal ions included in the mixture of alkali metal salts with protons. In addition, in the case where a higher ion exchange rate is desired, the alkali metal ions may undergo a reaction repeatedly with the strongly acidic cation exchange resins.

The flow rate of the aqueous solution of the mixture of alkali metal salts is not particularly limited, but the liquid hourly space velocity (LHSV), a value obtained by dividing a volume velocity (m$^3$/hr) of the aqueous solution supplied by a volume (m$^3$) of a resin layer including the strongly acidic cation exchange resin, is preferably from 5 hr$^{-1}$ to 30 hr$^{-1}$, and more, preferably from 10 hr$^{-1}$ to 20 hr$^{-1}$. Within this range, the ion exchange efficiency is high.

By evaporating water from an aqueous solution which has been brought into contact with the strongly acidic cation exchange resin, it is possible to acquire a mixture of 5% by mole or less of bis(2-methylphenyl)(6-methyl-3-sulphophenyl)phosphine, 80% by mole or more of bis(6-methyl-3-sulphophenyl)(2-methylphenyl)phosphine, and 15% by mole or less of tris(6-methyl-3-sulphophenyl)phosphine, as a solid. This mixture will be hereinafter abbreviated as an ion exchanged mixture.

4. Ammonium Salt Forming Step

It is possible to derive a corresponding ammonium salt by allowing a sulpho group included in the ion exchanged mixture obtained in the ion exchange step to undergo a reaction with the same number of moles of a tertiary amine.

It is preferable that the ion exchanged mixture is dissolved in water, and from the viewpoint of reducing the amount of the solvent evaporated, the ion exchanged mixture is preferably used as an aqueous solution including 3% by mass to 25% by mass of the ion exchanged mixture.

The appropriate amount of the tertiary amine can be confirmed by potentiometric titration. In the case of adding excess tertiary amine, the excess tertiary amine may be evaporated.

The amount of tertiary amine used is preferably 1-fold by mole to 3-fold by mole, more preferably 1.1-fold by mole to 2-fold by mole, and still more preferably 1.1-fold by mole to 1.5-fold by mole of that of the sulpho groups included in the ion exchanged mixture.

By concentrating a solution obtained by reacting the ion exchanged mixture with the tertiary amine to dryness, a desired product as a solid can be isolated, and by evaporating a part of the water, a concentrated aqueous solution can be acquired or the solution may be used as it is.

By directly adding the tertiary amine to the aqueous solution of the ion exchanged mixture, and sufficiently mixing them at 10° C. to 30° C. over 0.5 hours to 3 hours, the reaction with the corresponding ammonium sufficiently proceeds.

Furthermore, as the tertiary amine, a tertiary amine having a total of 3 to 27 carbon atoms in alkyl groups bonded to one nitrogen atom is used.

Examples of the tertiary amine include trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-diclodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, N,N-dibenzylmonoethylamine, and trinonylamine, These may be used alone or as a mixture of two or more kinds thereof.

The total number of carbon atoms in groups bonded to one nitrogen atom is preferably from 3 to 24, more preferably from 5 to 24, still more preferably from 5 to 10, and particularly preferably from 5 to 7. Further, as the group bonded to one nitrogen atom, an alkyl group, an aryl group, and an aryl-substituted alkyl group are preferred, and an alkyl group is more preferred.

Among those, as the tertiary amine, triethylamine, N,N-dimethylisopropylamine, and trioctylamine are preferred, and from the viewpoints of easy availability and production cost, triethylamine and N,N-dimethylisopropylamine are more preferred.

By evaporating water from the reaction mixed solution after completion of the reaction, it is possible to acquire a mixture of 5% by mole or less of a bis(2-methylphenyl)(6-methyl-3-sulphonatophenyl)phosphine ammonium salt, 80% by mole or more of a bis(6-methyl-3-sulphonatophenyl)(2-methylphenyl)phosphine diammonium salt, and 15% by mole or less of a tris(6-methyl-3-sulphonatophenyl) phosphine triammonium salt, as a solid. This mixture will be hereinafter abbreviated as a mixture of ammonium salts.

In order to increase the content of the bis(6-methyl-3-sulphonatophenyl)(2-methylphenyl)phosphine diammonium salt in the mixture of ammonium salts, column chromatography using a mixed solvent including water, tetrahydrofuran, and the like as a mobile phase, which is passed through a column packed with silica gel, can be used. Alternatively, a method in which an aqueous solution of a mixture of alkali metal salts is prepared and washed with an organic solvent such as 2-butanone can also be used.

A palladium catalyst comprised of the bis(6-methyl-3-sulphonatophenyl)(2-methylphenyl)phosphine diammonium salt obtained as above, or a mixture containing the same, and a palladium compound is excellent as a catalyst for a telomerization reaction. Examples of the telomerization reaction include a reaction in which butadiene is reacted with water in the presence of a palladium catalyst, a tertiary amine, and carbon dioxide to obtain 2,7-octadien-1-ol. In the telomerization reaction, the selectivity for 2,7-octadien-1-ol is improved and the recovery of the palladium catalyst is high, and therefore, the industrial availability is very high.

Furthermore, preferred examples of the palladium compound include 0-valent palladium compounds such as bis(t-butylisonitrile)palladium (0), bis(t-amylisonitrile)palladium (0), bis(cyclohexylisonitrile)palladium (0), bis(phenylisonitrile)palladium (0), bis(p-tolylisonitrile)palladium (0), bis(2,6-dimethylphenylisonitrile)palladium (0), tris(dibenzylideneacetone) dipalladium (0), (1,5-cyclooctadiene)(maleic anhydride)palladium (0), bis(norbornene)(maleic anhydride)palladium (0), bis(maleic anhydride)(norbornene)palladium (0), (dibenzylideneacetone)(bipyridyl)palladium (0), (p-benzoquinone)(o-phenanthroline)palladium (0), tetrakis (triphenylphosphine)palladium (0), tris(triphenylphosphine) palladium (0), bis(tritolylphosphine)palladium (0), bis (trixylylphosphine)palladium (0), bis(trimesitylphosphine) palladium (0), bis(tritetramethylphenyl)palladium (0), and bis(trimethylmethoxyphenylphosphine)palladium (0); and divalent palladium compounds such as palladium (II) chloride, palladium (II) nitrate, tetraammine dichloropalladium (II), disodium tetrachlorpalladium (II), palladium (II) acetate, palladium (II) benzoate, palladium (II) α-picolinate, bis(acetylacetone)palladium (II), bis(8-oxyquinoline)palladium (II), bis(allyl)palladium (II), (η-allyl) (η-cyclopentadienyl)palladium (II), (η-cyclopentadienyl)(1,5-cyclooctadiene)palladium (II) tetrafluoroborate, bis(benzonitrile) palladium (II) acetate, di-µ-chlorodichlorobis (triphenylphosphine)dipalladium (II), bis(tri-n-butylphosphine)palladium (II) acetate, and 2,2-bipyridyl palladium (II) acetate.

Furthermore, in the case where the telomerization reaction is carried out industrially, a step of mixing the telomerization reaction liquid obtained in the telomerization reaction step with an organic solvent having a dielectric constant of 2 to 18 at 25° C., followed by performing phase separation in the presence of to carbon dioxide, thereby obtaining 2,7-octadien-1-ol from an organic phase (product separation step), and a step of recovering an aqueous phase including the palladium catalyst with high efficiency (catalyst recovery step) are preferably carried out. At this time, in the case of using the bis(6-methyl-3-sulphonatophenyl)(2-methylphenyl)phosphine diammonium salt or the mixture containing the same, of the present invention, as a raw material for a palladium catalyst, the selectivity for a desired product and the recovery of the palladium catalyst are higher, as compared with other palladium catalysts, and therefore, the production cost is reduced, which is thus preferable.

Furthermore, examples of the organic solvent having a dielectric constant of 2 to 18 at 25° C. include n-dodecane, cyclohexane, 1,4-dioxane, benzene, p-xylene, m-xylene, toluene, dibutyl ether, diisopropyl ether, propanenitrile, ethylphenyl ether, diethyl ether, methyl-t-butyl ether, cyclopentylmethyl ether, fluorobenzene, 2-methyltetrahydrofuran, tetrahydrofuran, 2-heptanone, 4-methyl-2-pentanone, cyclopentanone, 2-hexanone, 2-pentanone, cyclohexanone, 3-pentanone, and acetophenone. Further, the dielectric constant of the organic solvent is preferably from 3 to 10.

Examples

Hereinafter, the present invention will be described in more detail with reference to Examples, but the present invention is not limited to such Examples in any case.

Hereinafter, in the production of various water-soluble triarylphosphines, the production was carried out at room temperature, at normal pressure, or under a nitrogen atmosphere unless otherwise specified, and as the solvent, those which had been purged with nitrogen in advance were used.

In addition, the water-soluble triarylphosphine obtained by sulphonating triarylphosphine is a mixture of those in which the number of sulpho groups introduced is 1 to 3, and may further include oxides formed by oxidation of the phosphorus.

The composition ratios (mass ratios) thereof in the water-soluble triarylphosphine were quantified from peak areas of $^{31}P$ obtained by measurement using a nuclear magnetic resonance apparatus "AVANCE III 400 USPlus" (manufactured by Bruker BioSpin K. K.) with a dimethylsulphoxide-$d_6$ (hereinafter referred to as DMSO-$d_6$) solution prepared such that the concentration of the produced water-soluble triarylphosphine is 0.05 mol/L. The chemical shift of $^{31}P$ in this case is a value at 305 K in the case where the chemical shift of the DMSO-$d_6$ solution prepared to have a concentration of the is phosphoric acid of 0.05 mol/L is set to 0 ppm.

Furthermore, the structure of the water-soluble triarylphosphine is determined from the chemical shifts and the peak areas of $^{31}P$ and $^1H$ obtained by measurement using a nuclear magnetic resonance apparatus "AVANCE III 600 USPlus" (manufactured by Bruker BioSpin K. K.) with a deuterium oxide solution prepared to have a concentration of 10 mmol/L. The chemical shift of $^{31}P$ in this case is a value at 300 K in the case where the chemical shift of a deuterium oxide solution prepared to have a concentration of the phosphoric acid of 10 mmol/L is set to 0 ppm. The chemical shift of $^1H$ in this case is a value at 300 K in the case where the chemical shift of a deuterium oxide solution prepared to have a concentration of trimethylsilylpropanoic acid-$d_4$ (hereinafter abbreviated as TSP) of 5 mmol/L is set to 0 ppm.

Sodium ions were quantified using an atomic absorption spectrophotometer "AA-7000F" (manufactured by Shimadzu Corporation).

For the operation for purifying a desired product, a high performance liquid chromatographic system (manufactured by Nihon Waters K.K., DELTA 600 MULTI-SOLVENT Systems, 2998 Photodiode Array Detector, Column Heater, Chromatography Data Software Empower 1) was used. Further, as a reversed phase chromatography column, "TSK-gel ODS-80Ts" (particle diameter of 5 µm, inner diameter of 20 mm, and length of 250 mm) manufactured by Tosoh Corporation, was used.

Production of Water-Soluble Triarylphosphine

Example 1

Production of Bis(6-methyl-3-sulphophenyl)(2-methylphenyl)phosphine

A sulphonation reaction was carried out in a batch mode. A 50 L glass-lined reactor equipped with a thermometer, a stirring device, and a jacket was used. 9.84 kg of concentrated sulphuric acid at a concentration of 97.4% by mass was placed in the reactor and cooled to 16° C. under stirring. Subsequently, 10.91 kg (35.84 mol) of tris(2-methylphenyl)phosphine (hereinafter abbreviated as TOTP) was introduced thereinto over 1 hour so as to maintain the temperature at 30° C. or lower. Thereafter, 37.60 kg (131.50 mol in terms of sulphur trioxide) of fuming sulphuric acid containing 28% by mass of sulphur trioxide was added thereto over 3 hours, while controlling the liquid temperature such that it was in a range of 30° C. to 40° C. Subsequently, the flow path of fuming sulphuric acid was washed with 1 kg of concentrated sulphuric acid at a concentration of 97.4% by mass. The reaction was carried out at a liquid temperature of from 20° C. to 30° C. over 4 hours.

On the other hand, 70 kg of ion-exchanged water was placed in a 200 L glass-lined reactor equipped with a thermometer, a stirring device, and a jacket, and the total amount of the above sulphonation reaction liquid was transferred thereto over 1 hour. Further, the flow path of the sulphonation reaction liquid was washed with 10 kg of ion-exchanged water, and the resultant was added to the above diluted liquid. In addition, the liquid temperature was controlled such that it was in a range of 20° C. to 40° C., thereby acquiring 137.80 kg of a diluted sulphonation reaction liquid.

27.50 kg (7.15 mol in terms of phosphorous atoms) of a diluted sulphonation reaction liquid and 5 kg of ion-exchanged water were added to a 200 L glass-lined reactor equipped with a thermometer, a stirring device, and a jacket. 24.10 kg of an aqueous 30.2%-by-mass sodium hydroxide solution was supplied thereto over 3 hours while controlling the liquid temperature such that it as in a range of 10° C. to 30° C. Further, 1.66 kg of an aqueous 4%-by-mass sodium hydroxide solution was added thereto over 1.7 hours. Thus, a neutralized liquid at pH 7.99 was acquired.

The neutralized liquid as allowed to exist in the range of 80 kPa to 100 kPa at 35° C. to 65° C. and concentrated over 4.5 hours, and 37 kg of water was evaporated therefrom. 45 kg of methanol was added to the concentrate, followed by stirring at 40° C. for 1 hour. Further, the mixture was allowed to exist in the range of 4 kPa to 55 kPa at 40° C. to 55° C. and concentrated over 2.4 hours, and 45 kg of methanol was evaporated therefrom. 147 kg of methanol was added to the concentrate, followed by stirring at 40° C. to 60° C. for 1 hour. Thereafter, the mixture was cooled to 30° C. or lower.

The methanol solution was allowed to pass through a pressure filter made of SUS304 in which 5 kg of "Celpure (registered trademark) S1000" manufactured by Advanced Minerals Corporation, as a high-purity diatomite filter aid was placed, thereby acquiring a filtrate. In addition, the filter aid was washed with 30 kg of methanol and the filtrate was combined with the above filtrate.

The total amount of the above acquired methanol solution was put into a 100 L glass-lined reactor equipped with a thermometer, a stirring device, and a jacket, allowed to exist in the range of 4 kPa to 55 kPa at 40° C. to 55° C., and concentrated to dryness over 18 hours, thereby acquiring 3.56 kg of a white solid (hereinafter referred to as an acquisition 1).

The acquisition 1 was a mixture including 0.13 kg (0.33 mol) of a bis(2-methylphenyl)(6-methyl-3-sulphonatophenyl)phosphine sodium salt as a mono-form, 2.91 kg (5.72 mol) of a bis(6-methyl-3-sulphonatophenyl)(2-methylphenyl)phosphine disodium salt as a di-form, and 0.52 kg (0.85 mol) of a tris(6-methyl-3-sulphonatophenyl)phosphine trisodium salt as a tri-form.

From the viewpoint that 3.56 kg (6.90 mol in terms of phosphorous atoms) of the acquisition 1 could be acquired from 27.50 kg (7.15 mol in terms of phosphorous atoms) of a diluted sulphonation reaction liquid, the yield based on the phosphorous atoms ranging from the sulphonation step to the neutralization step was 96.5%.

A column made of an acrylic resin (100 mm in diameter and 760 mm in height), packed with 5 kg of a strongly acidic cation exchange resin "Dowex G-26", was prepared. 12 kg of an aqueous solution including the acquisition 1 at 8.6% by mass (1044.0 g in terms of the acquisition 1, 2023.4 mmol in terms of phosphorous atoms) was allowed to pass from the upper part of the column at a linear velocity of 9.3 m/hr to 12.5 m/hr. The obtained aqueous solution was concentrated to dryness in the range of 35° C. to 70° C. at 4 kPa to 55 kPa to obtain 914.5 g of a white solid (hereinafter referred to as an acquisition 2).

$^{31}$H-NMR (400 MHz, 305 K, DMSO-$d_6$, phosphoric acid, ppm) δ: bis(2-methylphenyl)(6-methyl-3-sulphophenyl)phosphine as a mono-form showed a peak at −28.72, bis(6-methyl-3-sulphophenyl)(2-methylphenyl)phosphine as a di-form showed a peak at −26.00, and tris(6-methyl-3-sulphophenyl)phosphine as a tri-form showed a peak at −18.85.

The acquisition 2 was a mixture containing 35.3 g (91.9 mmol, 4.73% by mole) of bis(2-methylphenyl)(6-methyl-3-sulphophenyl)phosphine, 749.4 g (1613.4 mmol, 83.01% by mole) of bis(6-methyl-3-sulphophenyl)(2-methylphenyl)phosphine, and 129.8 g (238.3 mmol, 12.26% by mole) of tris(6-methyl-3-sulphophenyl)phosphine.

According to the atomic absorption analysis of the acquisition 2, the sodium content included in the acquisition 2 was 23 ppm or less in terms of sodium atoms. From the viewpoint that the number of sulpho groups contained in 1.0 kg of the acquisition 2 was 4410.6 mmol and the content of the sodium atoms was 1.0 mmol, 99.98% by mole or more of the sulphonate groups had been converted to sulpho groups.

From the viewpoint that 914.5 g (1943.6 mmol in terms of phosphorous atoms) of an acquisition 2 could be acquired by using 1044.0 kg (2023.4 mmol in terms of phosphorous atoms) of the acquisition 1, the yield based on the phosphorous atoms in the ion exchange step was 95.5%.

Example 2

Purification of Bis(6-methyl-3-sulphophenyl)(2-methylphenyl)phosphine

Using a high performance liquid chromatographic system equipped with a reversed phase chromatography column, a mixed liquid containing 70% by mass of water and 30% by mass of acetonitrile as a mobile phase was passed through the system at 5.0 mL/minute in the state where a column oven temperature was controlled to be 40° C.

1 g of an aqueous solution including 1% by mass of the acquisition 2 of Example 1 was prepared, and injected. The photodiode array detector was set to 275 nm and a distillate with a retention time of 17.5 minutes to 20.0 minutes was recovered. This operation was repeated 10 times. The collected distillate was concentrated to dryness in the range of 35° C. to 70° C. and 4 kPa to 56 kPa to acquire 55.5 mg of bis(6-methyl-3-sulphophenyl)(2-methylphenyl)phosphine as a white solid.

$^{31}$P-NMR (400 MHz, 305 K, DMSO-d$_6$, phosphoric acid, ppm) δ: −26.00 (s)

$^{31}$P-NMR (600 MHz, 300 K, deuterium oxide, phosphoric acid, ppm) δ: −24.69 (s)

$^1$H-NMR (600 MHz, 300 K, deuterium oxide, TSP, ppm) δ: 2.35 (s, 9 H), 6.84 (t, 6.2 Hz, 1 H), 7.18 (t, 7.6 Hz, 1 H), 7.21 (dd, 2.8 Hz, 1.8 Hz, 2 H), 7.35 (t, 6.3 Hz, 1 H), 7.41 (t, 7.4 Hz, 1 H), 7.45 (dd, 3.2 Hz, 4.7 Hz, 2 H), 7.80 (dd, 6.1 Hz, 1.8 Hz, 2 H)

From the viewpoint that 55.5 mg (0.118 mmol in terms of phosphorous atoms) of a desired product could be acquired by using 100.0 mg (0.213 mmol in terms of phosphorous atoms) of the acquisition 2, the yield based on the phosphorous atoms in the purification was 55.6%.

Example 3

Production of Bis(6-methyl-3-sulphonatophenyl)(2-methylphenyl)phosphine di(triethylammonium) Salt 500 g of an aqueous solution including 10% by mass of the acquisition 2 of Example 1 was prepared. Further, this aqueous solution included 50.0 g of the acquisition 2 with 106.3 mmol in terms of phosphorous atoms and 221.4 mmol of sulpho groups. An aqueous solution of the acquisition 2 was placed in a 3-neck flask having an inner capacity of 1 L, equipped with a thermometer, a stirring device, a dropping funnel, and a nitrogen gas line, and 24.6 g (243.5 mmol) of triethylamine was added thereto through the dropping funnel, followed by stirring in the range of 20° C. to 30° C. over 1 hour, thereby performing a reaction.

Thereafter, the reaction liquid was concentrated to dryness in the range of 35° C. to 70° C. and 4 kPa to 56 kPa, thereby acquiring 68.2 g of a white solid (hereinafter referred to as an acquisition 3).

$^{31}$P-NMR (400 MHz, 305 K, DMSO-d$_6$, phosphoric acid, ppm) δ: a bis(2-methylphenyl)(6-methyl-3-sulphonatophenyl)phosphine triethylammonium salt as a mono-form showed a peak at −28.12, a bis(6-methyl-3-sulphonatophenyl)(2-methylphenyl)phosphine di(triethylammonium) salt as a di-form showed a peak at −25.00, and a tris(6-methyl-3-sulphonatophenyl)phosphine tri(triethylammonium) salt as a tri-form showed a peak at −19.98.

The acquisition 3 was a mixture containing 2.3 g (4.7 mmol, 4.73% by mole) of a bis(2-methylphenyl)(6-methyl-3-sulphonatophenyl)phosphine triethylammonium salt, 55.5 g (83.2 mmol, 82.99% by mole) of a bis(6-methyl-3-sulphonatoephenyl)(2-methylphenyl)phosphine di(triethylammonium) salt, and 10.4 g (12.3 mmol, 12.28% by mole) of a tris(6-methyl-3-sulphonatophenyl)phosphine tri(triethylammonium) salt.

From the viewpoint that 68.2 g (100.2 mmol in terms of phosphorous atoms) of the acquisition 3 could be acquired by using 50.0 g (106.3 mmol in terms of phosphorous atoms) of the acquisition 2, the yield based on the phosphorous atoms in the ammonium salt forming step was 94.3%.

Example 4

Purification of Bis(6-methyl-3-sulphonatophenyl)(2-methylphenyl)phosphine di(triethylammonium) Salt 100 g of an aqueous solution including 50% by mass of the acquisition 3 of Example 3 was prepared. Further, the present aqueous solution included 50.0 g of the acquisition 3 with 73.5 mmol in terms of phosphorous atoms. An aqueous solution of the acquisition 3 was placed in a 3-neck flask having an inner capacity of 300 L, equipped with a thermometer, a stirring device, a dropping funnel, and a nitrogen gas line. To an aqueous solution of the acquisition 3 was added 100 g of 2-butanone, followed by stirring for 30 minutes, and the mixture was left to stand for 30 minutes, and an operation of removing a 2-butanone phase was repeated three times. By concentrating the obtained aqueous phase to dryness in the range of 35° C. to 70° C. and 4 kPa to 56 kPa, 41.7 g of a white solid was acquired.

The acquisition was a mixture containing 0.5 g (1.0 mmol, 1.69% by mole) of a bis(2-methylphenyl)(6-methyl-3-sulphonatophenyl)phosphine triethylammonium salt, 34.1 g (51.2 mmol, 84.53% by mole) of a bis(6-methyl-3-sulphonatophenyl)(2-methylphenyl)phosphine di(triethylammonium) salt, and 7.1 g (8.3 mmol, 13.78% by mole) of a tris(6-methyl-3-sulphonatophenyl)phosphine tri(triethylammonium) salt.

From the viewpoint that 41.7 g (60.5 mmol in terms of phosphorous atoms) of a desired product could be acquired by using 50.0 g (73.5 mmol in terms of phosphorous atoms) of the acquisition 3, the yield based on the phosphorous atoms in the purification was 82.4%.

Example 5

Production of Bis(6-methyl-3-sulphonatophenyl)(2-methylphenyl)phosphine di(tri-n-octylammonium) Salt By carrying out the same operation as in Example 3 except that 86.1 g (243.5 mmol) of tri-n-octylamine was used instead of triethylamine, 123.0 g of a pale orange high-viscosity liquid was acquired.

$^{31}$P-NMR (400 MHz, 305 K, DMSO-d$_6$, phosphoric acid, ppm) δ: a bis(2-methylphenyl)(6-methyl-3-sulphonatophenyl)phosphine tri-n-octylammonium salt as a mono-form showed a peak at −28.60, a bis(6-methyl-3-sulphonatophenyl)(2-methylphonyl)phosphine di(tri-n-octylammonium) salt as a di-form showed a peak at −25.00, and a tris(6-methyl-3-sulphonatophenyl)phosphine tri(tri-n-octylammonium) salt as a tri-form showed a peak at −17.67.

The acquisition was a mixture containing 3.6 g (4.9 mmol, 4.80% by mole) of a bis(2-methylphenyl)(6-methyl-3-sulphonatophenyl)phosphine tri-n-octylammonium salt, 99.2 g (84.6 mmol, 82.87% by mole) of a bis(6-methyl-3-sulphonatophenyl)(2-methylphenyl)phosphine di(tri-n-octylamine) salt, and 20.2 g (12.6 mmol, 12.33% by mole) of a tris(6-methyl-3-sulphonatophenyl)phosphine tri(tri-n-octylammonium) salt.

From the viewpoint that 123.0 g (102.1 mmol in terms of phosphorous atoms) of a desired product could be acquired by using 50.0 g (106.3 mmol in terms of phosphorous atoms) of the acquisition 2, the yield based on the phosphorous atoms in the ammonium salt forming step was 96.0%.

Example 6

Production of Bis(6-methyl-3-sulphonatophenyl)(2-methylphenyl)phosphine di(dimethylisopropylammonium) Salt By carrying out the same operation as in Example 3 except that 21.2 g (243.5 mmol) of N,N-dimethylisopropylamine was used instead of triethylamine, 67.5 g of a white solid was acquired.

$^{31}$P-NMR (400 MHz, 305 K, DMSO-d$_6$, phosphoric acid, ppm) δ: a bis(2-methylphenyl)(6-methyl-3-sulphonatophenyl)phosphine dimethylisopropylammonium salt as a mono-form showed a peak at −28.17, a bis(6-methyl-3-sulphonatophenyl)(2-methylphenyl)phosphine di(dimethylisopropylammonium) salt as a di-form showed a peak at −25.25, and a tris(6-methyl-3-sulphonatophenyl)phosphine tri(dimethylisopropylammonium) salt as a tri-form showed a peak at −21.50.

The acquisition was a mixture containing 2.4 g (5.0 mmol, 4.81% by mole) of a bis(2-methylphenyl)(6-methyl-3-sulphonatophenyl)phosphine dimethylisopropylammonium salt, 54.8 g (85.9 mmol, 82.85% by mole) of a bis(6-methyl-3-sulphonatophenyl)(2-methylphenyl)phosphine di(dimethylisopropylammonium) salt, and 10.3 g (12.8 mmol, 12.34% by mole) of a tris(6-methyl-3-sulphonatophenyl)phosphine tri(dimethylisopropylammonium) salt.

From the viewpoint that 67.5 g (103.6 mmol in terns of phosphorous atoms) of a desired product could be acquired by using 50.0 g (106.3 mmol in terms of phosphorous atoms) of the acquisition 2, the yield based on the phosphorous atoms in the ammonium salt forming step was 97.5%.

Telomerization Reaction

Hereinafter, it is shown that the water-soluble triarylphosphine of the present invention is useful for a telomerization reaction with reference to Reference Examples. Further, the present invention is not limited to such Reference Examples in any case.

Moreover, the concentrations of the palladium compounds and the phosphorus compounds included in the aqueous phase acquired by an extraction operation were quantified by subjecting a wet decomposition product to analysis using a polarized Zeeman atomic absorption spectrophotometer "Z-5300 Type" (manufactured by Hitachi, Ltd.).

In addition, organic materials such as a tertiary amine and 2,7-octadien-1-ol included in the telomerization reaction liquid or the aqueous phase including the palladium catalyst were analyzed and quantified by gas chromatography under the following measurement conditions.

Analysis Conditions for Gas Chromatography

Apparatus: GC-14 A (manufactured by Shimadzu Corporation)
Column used: G-300 (1.2 mm in internal diameter×20 m in length, and a film thickness of 2 μm),
(Materials) manufactured by Chemicals Evaluation, and Research Institute, Japan
Analysis conditions: an inlet temperature of 220° C. and a detector temperature of 220° C.
Sample injection amount: 0.4 μL
Carrier gas: helium (260 kPa) is flowed at 10 mL/minute.
Column temperature: maintained at 60° C. for 5 minutes→raised at 10° C./minute→maintained at 220° C. for 9 minutes
Detector: hydrogen flame ionization detector (FID)

Reference Example 1

The telomerization reaction was carried out in a batch mode. A 3 L autoclave equipped with a SUS316 electromagnetic induction stirring device including a 96 mL pressure container made of glass, for pumping a palladium catalyst, a 96 mL pressure container made of glass, for pumping a solvent, and a sampling port was used as a reactor. Further, the reaction was carried out at a stirring rotation speed of 500 rpm, and from the viewpoint that the reaction results at this time were not different from those at 1,000 rpm, a sufficient stirring state could be achieved.

17.69 g of a tetrahydrofuran solution including 94.74 mg (0.422 mmol in terms of palladium atoms) of palladium (II) acetate, and then 21.46 g of an aqueous solution including 1.440 g (2.116 mmol in terms of trivalent phosphorous atoms) of the phosphorous compound obtained in Example 3 were introduced into a pressure container made of glass and stirred for 60 minutes to prepare a palladium catalyst liquid.

30.06 g of distilled water, 80.10 g of triethylamine, 97.50 g of 2,7-octadien-1-ol, and 114.95 g (2.13 mol) of butadiene were put into the autoclave, followed by stirring at 500 rpm in a closed system and warming to 70° C. Thereafter, the palladium catalyst liquid was pumped from the pressure container made of glass through carbon dioxide within 10 seconds, while the total pressure was set to 1.2 MPa (gauge pressure). Further, a time point at which pumping of the palladium catalyst liquid was completed was defined as 0 hours at initiation of reaction.

In addition, the ratio of the trivalent phosphorus atoms to the palladium atoms at a time of preparation of a catalyst was 5.01, and in the telomerization reaction, the amount of the palladium atoms with respect to 1 mol of butadiene was 0.198 mmol, the mass ratio of triethylamine to water was 1.55, and the mass ratio of a mixture of butadiene and 2,7-octadien-1-ol to water was 4.12.

For the telomerization reaction liquid after a predetermined reaction time, the product was quantified by gas chromatography analysis.

The conversion of the butadiene was calculated by the following Equation 1. Further, the respective units in the equations are mol.

$$\text{Butadiene conversion (\%)}=100\times\{1-(\text{Amount of butadiene in reaction liquid/Amount of butadiene introduced})\} \quad \text{[Equation 1]}$$

Examples of the respective products include 2,7-octadien-1-ol, 1,7-octadien-3-ol, 1,3,6-octatriene, 1,3,7-octatriene, 2,4,6-octatriene, and 4-vinylcyclohexene. However, 1,3,6-octatriene, 1,3,7-octatriene, and 2,4,6-octatriene are collectively referred to as octatrienes. The selectivities of the respective products were calculated by the following Equation 2. Further, the respective units in the equations are mol.

$$\text{Selectivity for each product (\%)}=50\times(\text{Amount of each product in reaction liquid/Amount of butadiene reacted}) \quad \text{[Equation 2]}$$

The selectivities for high-boiling-point products which could not be sufficiently quantified by gas chromatography were calculated by the following Equation 3. Further, the respective units in the equations are mol.

$$\text{Selectivity for high-boiling-point product (\%)}=100-(\text{Total sum of selectivities of the respective products, calculated by Equation 2}) \quad \text{[Equation 3]}$$

After 8 hours of the reaction, the butadiene conversion was 81.6%, the selectivity for 2,7-octadien-1-ol was 92.5%, the selectivity for 1,7-octadien-3-ol was 3.2%, the selectivity for octatrienes was 2.6%, and the selectivity for the high-boiling-point products was 1.7%. Further, the selectivity for 4-vinylcyclohexene was 0.01% or less.

The autoclave was cooled to 25° C., and a reaction consumption-equivalent amount of water and 330.23 g (a volume at 25° C. of 463.2 mL) of diethyl ether were pumped through carbon dioxide, using a 96 mL pressure container made of glass, for pumping a solvent. The mixture was stirred for 1 hour while being pressurized to a total pressure of 3 MPa (gauge pressure) with carbon dioxide. This mixed liquid was transferred to a pressure container equipped with a glass window, which had been pressurized to 3 MPa (gauge pressure) with carbon dioxide using a pump, to carry out phase separation. The aqueous phase was suitably recovered into a pressure container made of glass, which had been pressurized to 1 MPa (gauge pressure) with carbon dioxide, connected to a pressure container equipped with a glass window. The pressure container made of glass was taken out, separated, and opened at normal pressure, and the weight of the aqueous phase was measured, while the acquired aqueous phase was used for various types of analysis.

In addition, the mass ratio of diethyl ether to the telomerization reaction liquid was 0.84.

The content of palladium included in the aqueous phase was calculated from the concentration of palladium as demonstrated by the analysis with a polarized Zeeman atomic absorption spectrophotometer using a wet decomposition product of the aqueous phase and the weight of the recovered aqueous phase. The recovery of the palladium atoms was calculated by the following Equation 4. Further, the units of the respective amounts in the equations are mol.

Recovery of palladium atoms (%)=(Amount of palladium in aqueous phase/Amount of palladium introduced)×100   [Equation 4]

The content of phosphorous included in the aqueous phase was calculated from the concentration of phosphorous as demonstrated by the analysis with a polarized Zeeman atomic absorption spectrophotometer using a wet decomposition product of the aqueous phase and the weight of the recovered aqueous phase. The recovery of the water-soluble triarylphosphine was calculated by the following Equation 5. Further, the units of the respective amounts in the equations are mol.

Recovery of water-soluble triarylphosphine (%)=100×(Amount of phosphorous atoms in aqueous phase/Amount of phosphorous atoms introduced)   [Equation 5]

The tertiary amine included in the aqueous phase was quantified by analyzing the aqueous phase using gas chromatography. The recovery of the tertiary amine was calculated by the following Equation 6. Further, the units of the respective amounts in the equations are mol.

Recovery of tertiary amine (%)=100×(Amount of tertiary amine in aqueous phase/Amount of tertiary amine introduced)   [Equation 6]

The recovery of the palladium atoms into the aqueous phase was 87.6%, the recovery of phosphorous atoms was 80.7%, and the recovery of triethylamine was 70.1%. Further, the amount of diethyl ether incorporated into the aqueous phase was 0.1% by mass or less.

Reference Example 2

The same operation as in Reference Example 1 except that 1.457 g (2.115 mmol in terms of trivalent phosphorous atoms) of the phosphorous compound obtained in Example 4 was used instead of the phosphorous compound obtained in Example 3 was carried out. Further, the ratio of the trivalent phosphorous atoms to the palladium atoms at a time of preparation of the catalyst was 5.01.

After 8 hours of the reaction, the butadiene conversion was 80.2%, the selectivity for 2,7-octadien-1-ol was 92.7%, the selectivity for 1,7-octadien-3-ol was 3.1%, the selectivity for octatrienes was 2.5%, and the selectivity for the high-boiling-point products was 1.7%. Further, the selectivity for 4-vinylcyclohexene was 0.01% or less.

The recovery of the palladium atoms into the aqueous phase was 88.9%, the recovery of phosphorous atoms was 84.6%, and the recovery of triethylamine was 70.8%. Further, the amount of diethyl ether incorporated into the aqueous phase was 0.1% by mass or less.

Reference Example 3

The same operation as in Reference Example 1 except that 2.545 g (2.113 mmol in terms of trivalent phosphorous atoms) of the phosphorous compound obtained in Example 5 was used instead of the phosphorous compound obtained in Example 3 was carried out. Further, the ratio of the trivalent phosphorous atoms to the palladium atoms at a time of preparation of the catalyst was 5.01.

After 6 hours of the reaction, the butadiene conversion was 74.4%, the selectivity for 2,7-octadien-1-ol was 93.1%, the selectivity for 1,7-octadien-3-ol was 3.1%, the selectivity for octatrienes was 2.7%, and the selectivity for the high-boiling-point products was 1.1%. Further, the selectivity for 4-vinylcyclohexene was 0.01% or less.

The recovery of the palladium atoms into the aqueous phase was 86.9%, the recovery of phosphorous atoms was 76.8%, and the recovery of triethylamine was 76.9%. Further, the amount of diethyl ether incorporated into the aqueous phase was 0.1% by mass or less.

The same operation as in Reference Example 1 except that 2.120 g (2.120 mmol in terms of trivalent phosphorous atoms) of a diphenyl(3-sulphonatophenyl)phosphine triethylammonium salt (with a provision that it included 4.40% by mole of oxides) was used instead of the phosphorous compound obtained in Example 3 was carried out. Further, the ratio of the trivalent phosphorous atoms to the palladium atoms at a time of preparation of the catalyst was 5.02.

After 4 hours of the reaction, the butadiene conversion was 77.6%, the selectivity for 2,7-octadien-1-ol was 88.2%, the selectivity for 1,7-octadien-3-ol to was 5.1%, the selectivity for octatrienes was 5.1%, and the selectivity for the high-boiling-point products was 1.6%. Further, the selectivity for 4-vinylcyclohexene was 0.01% or less.

The recovery of the palladium atoms into the aqueous phase was 28.2%, the recovery of phosphorous atoms was 48.8%, and the recovery of triethylamine was 65.5%. Further, the amount of diethyl ether incorporated into the aqueous phase was 0.1% by mass or less.

Reference Example 5 (Comparative)

The same operation as in Reference Example 1 except that 1.015 g (2.113 mmol in terms of trivalent phosphorous atoms) of a diphenyl(6-methyl-3-sulphonatophenyl)phosphine triethylammonium salt (with a provision that it included it included 4.58% by mole of oxides) was used instead of the phosphorous compound obtained in Example 3 was carried out. Further, the ratio of the trivalent phosphorous atoms to the palladium atoms at a time of preparation of the catalyst was 5.01.

After 4 hours of the reaction, the butadiene conversion was 85.0%, the selectivity for 2,7-octadien-1-ol was 88.8%, the selectivity for 1,7-octadien-3-ol was 5.0%, the selectivity for octatrienes was 4.4%, and the selectivity for the high-boiling-point products was 1.8%. Further, the selectivity for 4-vinylcyclohexene was 0.01% or less.

The recovery of the palladium atoms into the aqueous phase was 12.0%, the recovery of phosphorous atoms was 28.3%, and the recovery of triethylamine was 76.5%. Further, the amount of diethyl ether incorporated into the aqueous phase was 0.1% by mass or less.

According to Example 1, it is apparent that a mixture of 5% by mole or less of bis(2-methylphenyl)(6-methyl-3-sulphophenyl)phosphine, 80% by mole or more of bis(6-methyl-3-sulphophenyl)(2-methylphenyl)phosphine, and 15% by mole or less of tris(6-methyl-3-sulphophenyl)phosphine can be acquired with high yield.

Furthermore, according to Example 2, it is apparent that bis(6-methyl-3-sulphophenyl)(2-methylphenyl)phosphine can be isolated and purified by column chromatography.

According to Examples 3, 5, and 6, it is apparent that a bis(6-methyl-3-sulphonatophenyl)(2-methylphenyl)phosphine diammonium salt can be acquired with high yield by reacting bis(6-methyl-3-sulphophenyl)(2-methylphenyl)phosphine with a tertiary amine having a total of 3 to 27 carbon atoms in groups bonded to one nitrogen atom.

According to Example 4, it is apparent that the bis(6-methyl-3-sulphonatophenyl)(2-methylphenyl)phosphine diammonium salt can be made to have increased purity by washing with a ketone solvent or the like.

According to Reference Examples 1 to 5, it is apparent that the bis(6-methyl-3-sulphonatophenyl)(2-methylphenyl) phosphine diammonium salt provided by the present invention can be obtained with higher selectivity in the telomerization reaction and the recovery of the palladium catalyst is higher, as compared with other water-soluble triarylphosphines, and therefore, it is useful when carrying out industrial telomerization reactions.

INDUSTRIAL APPLICABILITY

The bis(6-methyl-3-sulphonatophenyl)(2-methylphenyl) phosphine diammonium salt obtained by using bis(6-methyl-3-sulphophenyl)(2-methylphenyl)phosphine of the present invention is useful for a telomerization reaction of two molecules of an alkadiene such as butadiene with a nucleophilic reactant such as water.

The invention claimed is:

1. A method of performing a telomerization reaction, consisting essentially of:
   reacting an alkadiene comprising butadiene with water in the presence of a bis(6-methyl-3-sulphonatophenyl)(2-methylphenyl)phosphine diammonium salt, palladium compound, a tertiary amine, and carbon dioxide,
   wherein the bis(6-methyl-3-sulphonatophenyl)(2-methylphenyl)phosphine diammonium salt is obtained by reacting bis(6-methyl-3-sulphophenyl)(2-methlyphenyl)phosphine with a tertiary amine having a total of 3 to 27 carbon atoms in groups bonded to one nitrogen atom, and
   wherein in a product of the reacting of the alkadiene with water, a molar ratio of 2,7-octadien-1-ol to a total of 2,7-octadien-1-ol and 1,7-octadien-3-ol is at least 96.7%.

2. The method of claim 1, wherein the tertiary amine is selected from the group consisting of trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, N,N-dibenzylmonoethylamine, and trinonylamine.

3. The method of claim 2, wherein the tertiary amine reacted with bis(6-methyl-3-sulphophenyl)(2-methlyphenyl)phosphine is trioctylamine.

4. The method of claim 1, wherein the tertiary amine reacted with bis(6-methyl-3-sulphophenyl)(2-methlyphenyl)phosphine has a total of 5 to 10 carbon atoms in groups bonded to one nitrogen atom.

5. The method of claim 4, wherein the tertiary amine reacted with bis(6-methyl-3-sulphophenyl)(2-methlyphenyl)phosphine is selected from the group consisting of triethylamine, tripropylamine, triisopropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, and N,N-dimethyloctylamine.

6. The method of claim 1, wherein the tertiary amine reacted with bis(6-methyl-3-sulphophenyl)(2-methlyphenyl)phosphine has a total of 5 to 7 carbon atoms in groups bonded to one nitrogen atom.

7. The method of claim 6, wherein the tertiary amine reacted with bis(6-methyl-3-sulphophenyl)(2-methlyphenyl)phosphine is selected from the group consisting of triethylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, and N,N-dimethylneopentylamine.

8. The method of claim 7, wherein the tertiary amine reacted with bis(6-methyl-3-sulphophenyl)(2-methlyphenyl)phosphine is triethylamine.

9. The method of claim 7, wherein the tertiary amine reacted with bis(6-methyl-3-sulphophenyl)(2-methlyphenyl)phosphine is N,N-dimethylisopropylamine.

10. A method of performing a telomerization reaction, comprising:

reacting an alkadiene comprising butadiene with water in the presence of a bis(6-methyl-3-sulphonatophenyl)(2-methylphenyl)phosphine diammonium salt, palladium compound, a tertiary amine, and carbon dioxide, wherein the bis(6-methyl-3-sulphonatophenyl)(2-methylphenyl)phosphine diammonium salt is obtained by reacting bis(6-methyl-3-sulphophenyl)(2-methlyphenyl)phosphine with a tertiary amine having a total of 3 to 27 carbon atoms in groups bonded to one nitrogen atom, and wherein in a product of the reacting of the alkadiene with water, a molar ratio of 2,7-octadien-1-ol to a total of 2,7-octadien-1-ol and 1,7-octadien-3-ol is at least 96.7%.

11. The method of claim 10, wherein a noble metal is present during the reacting of the alkadiene with water.

12. The method of claim 11, wherein the noble metal comprises palladium.

13. The method of claim 12, further comprising:
recovering the palladium; and
reusing the recovered palladium in the reacting of the alkadiene with water.

14. The method of claim 10, wherein triethylamine is present during the reacting of the alkadiene with water.

* * * * *